(12) United States Patent
Robioneck et al.

(10) Patent No.: US 6,296,647 B1
(45) Date of Patent: Oct. 2, 2001

(54) INSTRUMENT FOR THE POSITIONING OF AN IMPLANT IN THE HUMAN SPINE

(75) Inventors: Bernd Robioneck, Preetz; Christian Lutz, Bovenau, both of (DE); Reinhard Windhager; Rainer Kotz, both of Vienna (AU); Richard Vlasak, Gainesville, FL (US); Paul Wuisman, Amsterdam (NL)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 09/369,477

(22) Filed: Aug. 6, 1999

(30) Foreign Application Priority Data

Aug. 7, 1998 (DE) .......................................... 298 14 174 U

(51) Int. Cl.[7] .............................. A61F 2/46; A61B 17/70; A61B 17/66
(52) U.S. Cl. .............................. 606/105; 606/90; 606/61; 623/17.11
(58) Field of Search .............................. 606/61, 90, 105; 623/17.11, 17.12, 17.13, 17.14, 17.15, 17.16; 600/231, 232, 233, 235

(56) References Cited

U.S. PATENT DOCUMENTS

| | | | |
|---|---|---|---|
| 5,219,349 | * 6/1993 | Krag et al. ......................... | 606/53 |
| 5,397,364 | * 3/1995 | Kozak et al. ....................... | 623/17 |
| 5,458,641 | * 10/1995 | Ramirez Jimenez ................. | 623/17 |
| 5,674,296 | * 10/1997 | Bryan et al. ....................... | 623/17 |
| 5,776,197 | 7/1998 | Rabbe et al. ....................... | 623/17 |
| 5,836,948 | * 11/1998 | Zucherman et al. ................. | 606/61 |
| 5,885,284 | * 3/1999 | Errico et al. ...................... | 606/61 |
| 5,935,151 | * 8/1999 | Broughton et al. ................. | 606/241 |
| 6,033,438 | * 3/2000 | Bryan et al. ....................... | 623/17 |
| 6,106,557 | * 1/2001 | Robioneck et al. ................. | 623/17 |
| 6,159,244 | * 12/2000 | Suddaby ............................ | 623/17.11 |
| 6,174,334 | * 1/2001 | Suddaby ............................ | 623/17.11 |

FOREIGN PATENT DOCUMENTS

| | | |
|---|---|---|
| 43 28 690 A1 | 3/1995 | (DE) . |
| 44 38 264 C2 | 3/1996 | (DE) . |
| 296 23 246 U 1 | 2/1998 | (DE) . |
| 296 23 247 U 1 | 4/1998 | (DE) . |
| 0 567 424 A1 | 10/1993 | (EP) . |
| WO 98/04202 | 2/1998 | (WO) . |

* cited by examiner

Primary Examiner—Gene Mancene
Assistant Examiner—Michael B. Priddy
(74) Attorney, Agent, or Firm—Lerner, David, Littenberg, Krumholz & Mentlik, LLP

(57) ABSTRACT

An instrument for the positioning of an implant into the human spine, as a replacement for one or more diseased vertebra bodies has vertebra body plates attachable to the healthy vertebra bodies. Distraction rods are provided which at one end are attachable to a vertebra body plate. Two U-shaped parts having limbs which telescopically cooperate and form a tubular housing around the attached distraction rods. The U-shaped parts comprise inner sections which are supported on the distraction rods. A distraction instrument which is connectable to the other ends of the distraction rods is used for exerting a force onto the rods transversely to their longitudinal direction.

29 Claims, 4 Drawing Sheets

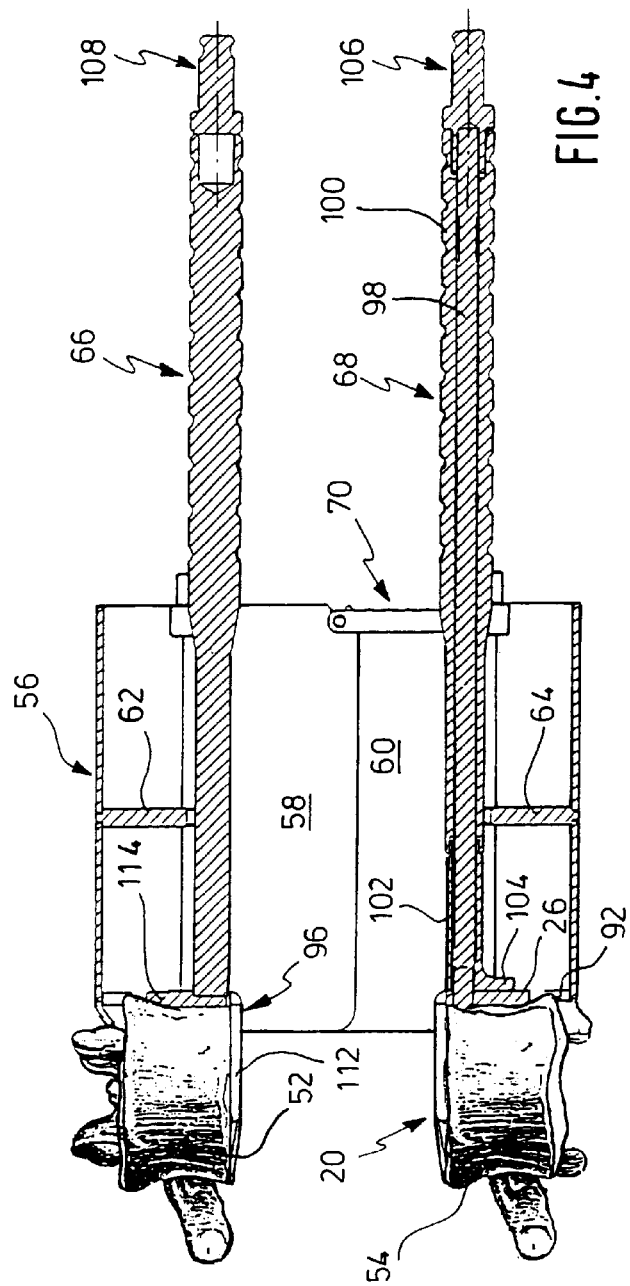
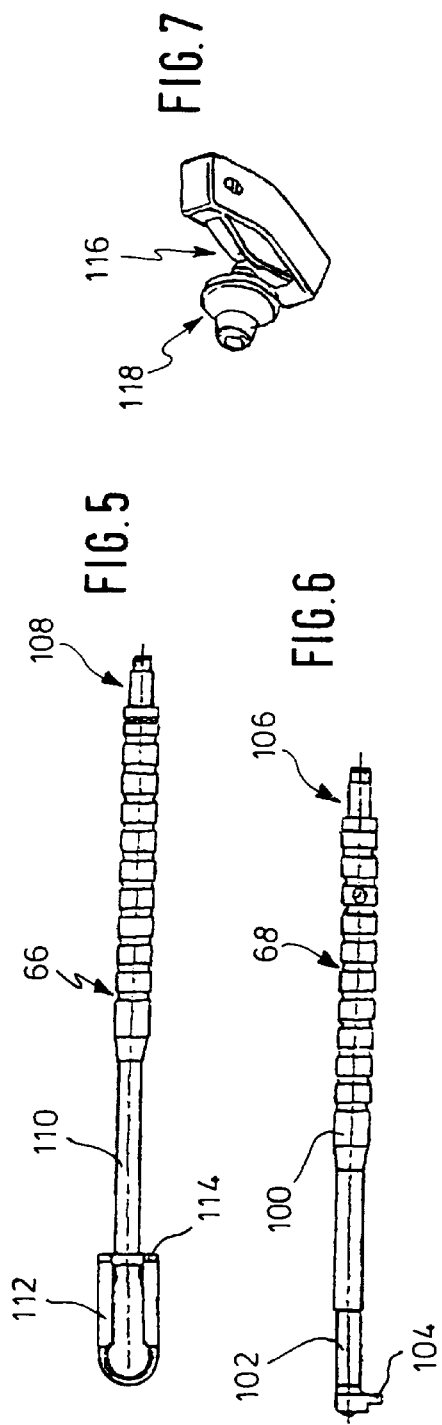

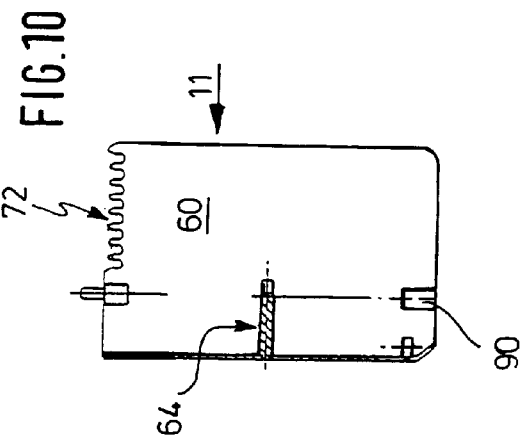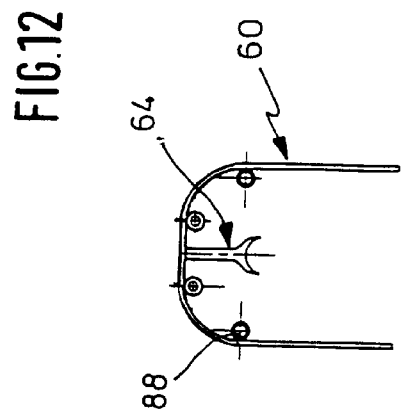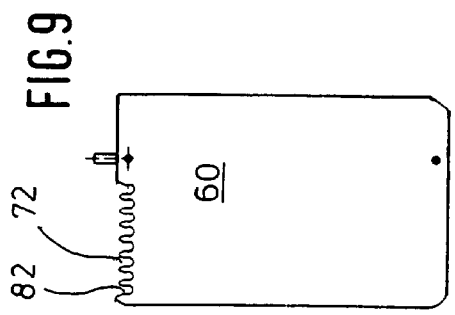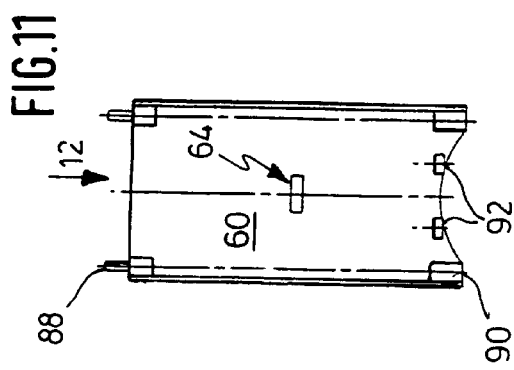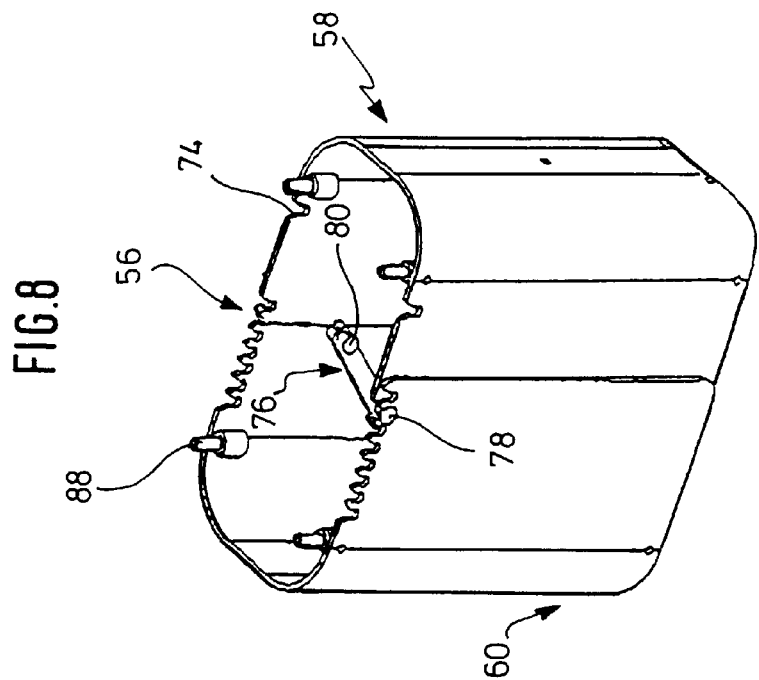

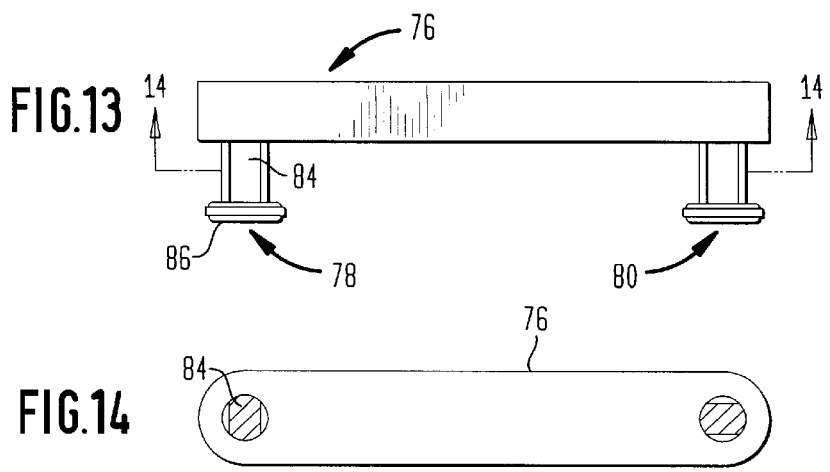
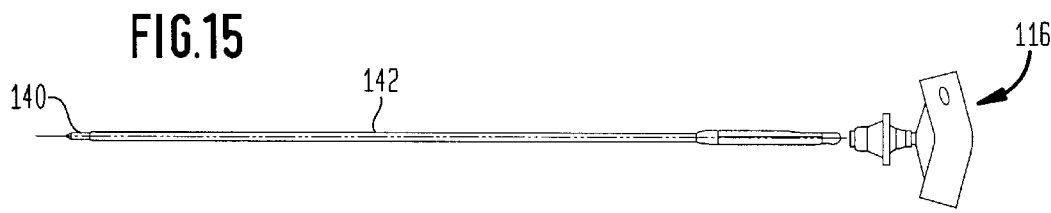
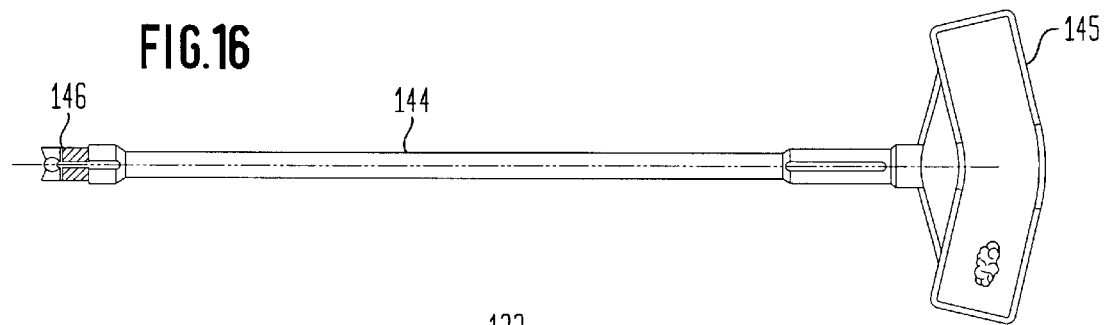
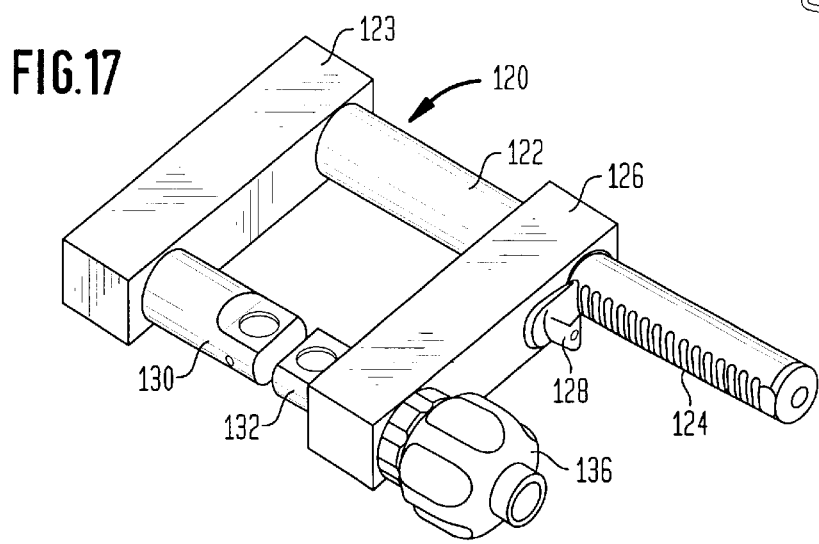

INSTRUMENT FOR THE POSITIONING OF AN IMPLANT IN THE HUMAN SPINE

BACKGROUND OF THE INVENTION

1. Field of the Invention.

The invention relates to an instrument for removing vertebra and positioning an implant in the human spine as a replacement for one or more vertebrae.

2. Discussion of the Prior Art.

With diseases of the human spine it is increasingly necessary to remove one or more vertebra or vertebral bodies. After the removal a replacement implant must be inserted which assumes the load on the spine. To accomplish this, various devices are known. Primarily, cage-like bodies are utilized which are adapted to the shape of the vertebra body and leave adequate possibilities for the bone material to grow in. Additionally it is however necessary to attach a stabilizing implant which rigidly connects bordering healthy vertebra bodies to one another. The vertebra body space retainers although mostly in the position to transmit pressure forces, may however not carry out a lateral stabilization.

The implantation of such implants is effected from the front side of the patient, wherein the implant is inserted laterally into the spine. Before the insertion, as mentioned a clearing out of the diseased vertebra body and a dissection of the invertebral disc is required. With the present invention an instrument is created for the implantation of such implants in a way and manner which is simple as possible and which is gentle on the patient. Furthermore there is to be created a possibility of setting the healthy vertebral body or keeping it at a distance during the preparation work.

SUMMARY OF THE INVENTION

With the instrumentation according to the invention there are provided vertebra body plates which may be attached to the healthy vertebra body. The vertebra body plates may be part of the implant to be implanted, or plates attached separately to a rod. In this case, the plates temporarily may be brought into engagement with the healthy vertebra body and then removed. The instrumentation according to the invention further envisages distraction rods which are connectable at one end to each of the vertebra body plates. In the case of a removable plate the plate may be formed as one piece with the distraction rod. If the vertebra body plate is formed as part of the final implant the distraction rod is a separate piece and is preferably connected to the vertebra plate via a threaded connection.

The instrumentation according to the invention further envisages two U-shaped parts, whose limbs cooperate in a telescopic manner and form a tubular housing around the already attached distraction rods, wherein the U-shaped parts comprise inner sections which are supported on the distraction rods. The U-shaped parts or the tubular housing formed by them forms a type of tunnel which keeps soft parts away from the operating region and permits an access without hindrance to the operating region.

Finally there is provided a distraction instrument which is connectable to the other end of the distraction rods opposite the vertebra body plates for applying a force onto the rods transversely to their longitudinal extension. In this manner the vertebrae may be moved apart or the distance between the vertebrae may be retained.

According to one embodiment of the invention there are two vertebra plates which are formed approximately L-shaped with a first limb which bears against an end surface of the vertebral column or on the invertebral disk and with a second limb which bears on the circumferential surface of the vertebra body and which can be attached to this by a screw. The second limb comprises a threaded hole for screwing it to a distraction rod or an implant rod. Both plates may be identical.

In order to create the possibility of attaching a vertebra plate quite early to the healthy vertebra body or of setting the healthy vertebra, before the replacement implant is inserted, in another embodiment of the invention it is useful when a section of the replacement implant, which faces a vertebra body, comprises a receiving section and the first limb of the vertebra plate and the receiving section are formed such that the replacement implant may be inserted into a space cleared of one or more vertebra bodies whilst the vertebra plates are already attached to bone. For example the cooperating sections may comprise dovetail guides so that in the axial direction a secure connection between the vertebra plate and replacement implant is created.

Such an implant is described in our copending application Ser. No. 09/369,271 filed Jul. 22, 1999, the teachings of which are incorporated herein by reference.

So that no unnecessary injuries may take place the web of the U-shaped parts are curved outwardly in a circular arc shaped manner. According to another embodiment of the invention on the inner side they comprise a fork or jaw-shaped section which is supported on a distraction rod and may partially surround the same.

It is useful after adjustment that the U-shaped parts bearing on the distraction rib are fixed to one another in their position, since for the operation procedures it is also necessary to remove the distraction rods in order to carry out further manipulations. Therefore one embodiment of the invention envisages that on a lateral end edge of one limb a U-shaped part comprises a row of recesses and on the other U-shaped part there is linked a bar with a lateral peg which lockingly is introduceable into one of the recesses. The recesses may comprise a narrow location and the locking peg comprises an elongate cross section and is rotatably mounted in the bar. In the one rotational position the peg is therefore lockingly fixed in a recess, whilst in another position, for example rotated about 90°, it may be moved out of the recess.

According to another requirement it may also be necessary to lengthen the housing or the tunnel. One formation of the invention envisages that two or more pairs of U-shaped parts are provided which are formed so that they may be stuck onto one another.

A distraction frame according to a further embodiment of the invention is provided with two jaws of which one is attached to a connection piece in a rigid manner and the other adjustable in steps. Onto the jaws there are attached receiving pieces for the distraction rods, wherein the one receiving piece is adjustable with respect to the rigid receiving piece by way of a threaded spindle. In this manner a coarse and fine adjustment for the distraction procedure is created.

BRIEF DESCRIPTION OF THE DRAWINGS

Embodiment examples of the invention are hereinafter described in more detail by way of drawings.

FIG. 4 is a section through the housing according to FIG. 3 and the distraction rods leading to the healthy vertebrae;

FIG. 5 is a plan view of the upper distraction rod according to FIG. 4;

FIG. 6 is a lateral view of the lower distraction rod according to FIG. 4;

FIG. 7 is a perspective view of a grip for the rods according to the FIGS. 5 and 6;

FIG. 8 is a perspective view of the housing according to FIG. 4;

FIG. 9 is a lateral view of a U-shaped part of the housing according to FIG. 8;

FIG. 10 shows a section through the U-shaped part according to FIG. 9;

FIG. 11 is an elevation view of the U-shaped part of FIG. 10 in the direction of arrow 11.

FIG. 12 is a lateral view of the representation according to FIG. 11 in the direction of arrow 12;

FIG. 13 is a plan view of a bar of the housing according to FIG. 8;

FIG. 14 is a section through the representation according to FIG. 13 along the line 14—14;

FIG. 15 is a lateral view of an introduction rod for the replacement implant according to the FIGS. 1 and 2;

FIG. 16 is a lateral view of a driver for fastening a nut of the implant according to FIGS. 1 and 2; and FIG. 17 is a perspective view of a distraction instrument according to the invention.

DESCRIPTION OF THE PREFERRED EMBODIMENTS

Figure 1:
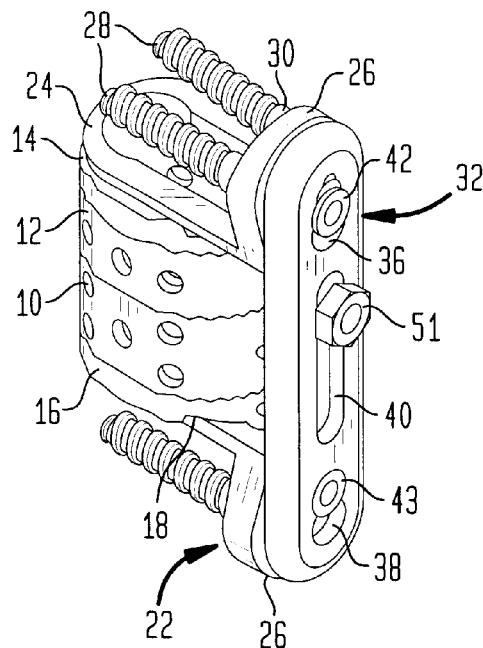
FIG. 1 is a perspective view of a replacement implant for one or more vertebra bodies of the human spine.
Figure 2:
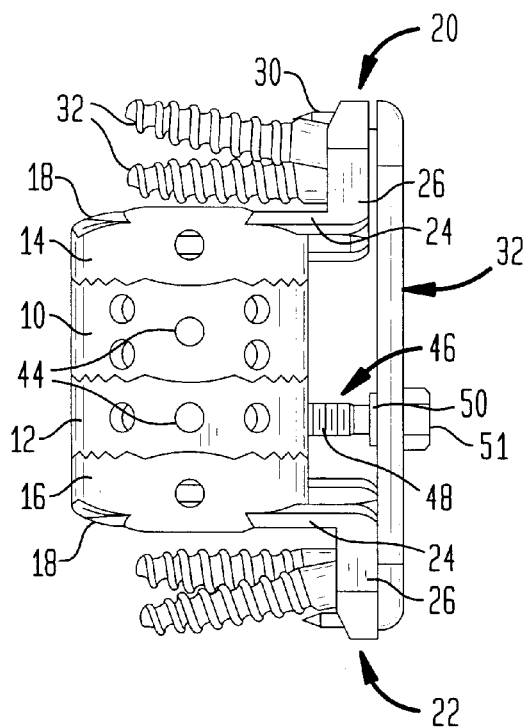
FIG. 2 is a lateral view of the replacement implant according to FIG. 1.

Referring to FIGS. 1 and 2, there is shown a replacement implant, for one or more vertebra bodies which is composed of several individual parts, specifically of an annular oval or elliptical middle body 10 and of a middle body 12 the same in contour but of a smaller height. Furthermore an upper end body 14 and a lower end body 16 are to be recognized. The bodies 10 to 16 are fittingly stacked over one another and may be fixed with respect to one another via suitable teeth running in the direction of the larger diameter of the oval. Furthermore clip-like pins may be arranged in bores of the individual bodies in order to fix these with respect to one another. The end bodies may comprise an inclined end surface or be shaped annular-cylindrical as the middle bodies 10, 12, wherein the inclination of the end surfaces may also be different. The bodies 10 to 16 may with this be formed in a modular manner, wherein for example the middle bodies may be provided in graded heights, whilst for example the end bodies have the same height but have differingly inclined free end surfaces.

In the preferred embodiment, the end bodies 14, 16 furthermore comprise on the free surfaces dovetail guides 18. Above and below the end bodies 14, 16 there are arranged vertebra plates 20, 22. They comprise a first limb 24 which comprises two distanced runners which at the free end are connected to one another. The runners form on the inner edges a dovetail profile which fittingly cooperates with the dovetail guide 18 so that the limb 14 may be fittingly inserted into the end body 14 or 16, as is represented in FIGS. 1 and 2. A plate-like limb 26 bent at right angles thereto comprises holes for accommodating bone screws 28 which are screwed into the healthy vertebra bodies for attaching and stabilizing the complete arrangement according to the FIGS. 1 and 2. Furthermore, in the preferred embodiment, the plate-like limbs comprise spikes 30 which face in the same direction as the first limb 24. The spikes dig themselves into the wall of the healthy vertebra.

A connection and compression plate 32 comprises at the ends a hole 36 or 38 and between the ends an elongate hole 40. The hole 36 is a so-called compression hole, i.e. it narrows in the direction of the end of the plate 32 so that with the help of a screw 42 which is screwed into a non-shown threaded hole of the limb 36, a relative movement between the plate 32 and the vertebra plate 20 is effected. The relative movement acts in the sense of a compression of the stack formed by the bodies 10 to 16.

The hole 38 consists in principle of two holes arranged next to one another for the purpose of adaptation to the differing height of the mentioned cage stack.

The middle bodies 10, 12 comprise on the circumference threaded holes 44, wherein the holes 44 are arranged on the middle circumferential line in each case at a circumferential distance of 90'. As can be recognized from FIG. 1, the arrangement of the vertebra plates 20, 22 and the plate 32 is such that they lie in the direction of the large diameter of the oval of the bodies 10 and 12. Accordingly there is located also a threaded hole 44 of the plate 32 lying opposite. Into this hole there may be screwed an adjusting screw 46 which comprises a first threaded section 48 and a second threaded section (which is not shown) and which extends through the elongate hole 40. Between the threaded sections there is located a radial collar 50 which bears against the inner side of the plate 32 (FIG. 2). A nut 51 is screwed onto the other part of the other threaded section, which is located on the other side of the plate 32. With the help of this arrangement the distance of the plate 32 to the cage stack may be adjusted.

This device is shown in more detail in our copending U.S. patent application.

Figure 3:
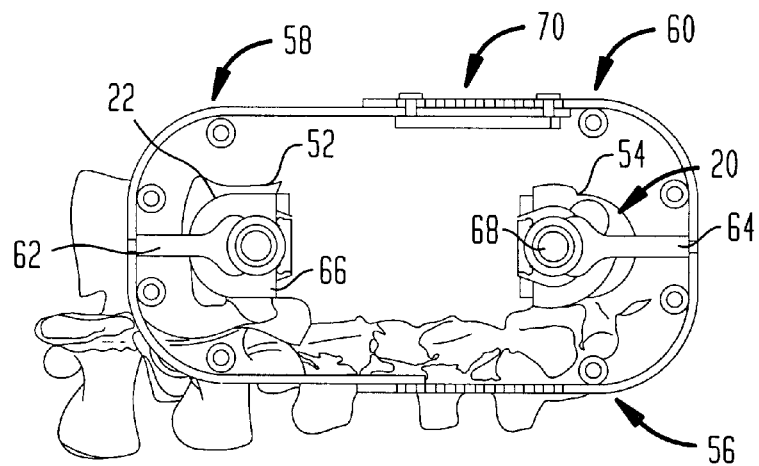
FIG. 3 is a lateral view of a part of the human spine with a tunnel-like or tube-like housing leading through to the operating region.

In FIG. 3 there is indicated a part of the human spine in the lumbar region, wherein between two healthy vertebra bodies 52, 54 there is effected a removal of one or two diseased vertebra bodies. In FIG. 3 it is further shown that two vertebra plates are attached in the above mentioned way and manner, wherein the plate 22 may also be part of an instrument which will be discussed further below and which is only temporarily connected to the vertebra body 52. One further recognizes in FIG. 3 a tunnel-like housing 56 which extends towards the operating region. It consists of two U-shaped parts of sheet material, whose limbs are inserted into one another in a telescopic manner. On the inner side of the web or wall of the U-shaped parts 58, 60 there are attached attachments 62, 64 with a jaw or opening at the free end which partly accommodates a distraction rod 66, 68. The attachments 62, 64 may be forked-shaped. The U-shaped parts 58, 60 are consequently supported on the rods 66, 68 in this manner. The parts 58, 60 are also mutually locked as is indicated at 70, which will be discussed in more detail below.

The construction of the housing 56 is shown in more detail in FIGS. 8 to 12. One recognizes that the limbs of the U-shaped part 60 comprise a row of recesses 72 on the lateral edge, which form part of a locking system 70. The limbs of the U-shaped part 58 comprise on the same side two spaced recesses 74. A bar 76 comprises pegs 78, 80 which cooperate with the recesses 72, 74 in order to fix the U-shaped parts 58, 60 in their position to one another. The recesses 72, 74 are formed such that they comprise a narrowed slot 82 with a wider portion thereunder. From the FIGS. 13 and 14 the construction of the bar 76 can be deduced more clearly. The pegs 78, 80 comprise a shank 84 and a somewhat larger head 86 at the free end. In FIG. 13 the pegs 78, 80 are shown rotated about 90° relative to one another. This is also to be recognized in FIG. 14. If the peg 78 in the position according to FIG. 14 is introduced into one of the recesses 72, 74 it may pass the narrow cross section 82 into the wider portion. If subsequently the peg 78 is rotated by 90° it is locked in the recess 72, 74. The same applies to peg 80. With the help of the bar 76 therefore the distance of the U-shaped parts 58, 60 to one another may be adjusted.

The U-shaped parts 58, 60 on the inner side of the limbs comprise upwardly standing pegs 88 and on the lower side mountings 90. Therefore pairs of U-shaped parts 58, 60 may be stuck onto one another. Furthermore the U-shaped parts 58, 60 on the side lying opposite the recesses 72 comprise eyes 92 for fastening the housing 56 to the vertebrae (See FIG. 4).

In FIG. 4 two rod embodiments are shown i.e. rod 66 and 68. Normally, two rods 66 or 68 would be used at the same time. On rod 66 there is attached an angular attachment plate 96 which is the same as the vertebra plate 20, 22 and which is placed on the vertebra body 52 in the same manner. As is subsequently explained in more detail the instrument 66 serves a preparatory operating procedure before the insertion of the replacement implant.

The rod 68 is connected to the vertebra plate 20. The rod 68 is constructed in a complex manner. It consists of an inner threaded rod 98 which at one end is screwed into the threaded hole of the second limb 26 in the-vertebra plate 20. The rod 98 extends through a hollow rod 100. Adjacent limb 26 the threaded rod 98 is surrounded by a sleeve section 102 which at its free end comprises a radial flange section 104. At one end the hollow rod 100 accommodates a section of a peg 106 which, as will yet be described, cooperates with a distraction apparatus. With the help of the peg 106 the threaded rod 98 may be screwed into the threaded hole. Peg 106 may have a female thread to receive an end of threaded rod 98. Once the peg 106 is tightened on the end of rod 98 further turning turns peg 106 and rod 98 in unison. Simultaneously, the rod 100 is pressed against the sleeve section 102 and thus the flange 104 against the limb 26. In this manner a force may be effectively transmitted onto the vertebra body 54. The described arrangement serves for attaching a vertebra plate 20 in the way and manner shown in FIG. 4, wherein subsequently the limb 26 is provisionally fixed on the vertebra body 54 with the help of a bone screw, and on the other hand serves the setting of the vertebra body 54.

Similar to the rod 68 there is provided a peg 108 which may be threaded on the rod 66 which creates a rotational connection to the rod 66 and is suitable for the application into the distraction apparatus.

The rod 66 is shown in FIG. 5 in a plan view. One recognizes that a continuous solid shank 110 at the end comprises two limbs 112, 114 which are arranged at right angles to one another and in their construction are roughly the same as a vertebra plate 20, 22. This particularly applies to the limb 112 which bears against the vertebra body or against the invertebral disk.

In FIG. 6 there is shown a plan view of the rod 68. One recognizes that a releasable handle 116 according to FIG. 7 is connectable to the rods 66, 68 or to the pegs 108, 106. For this purpose the handle 116 comprises a head 118 which can receive and hold pegs 106, 108. After inserting the rod 66 or 68 the handle 116 may be removed. Subsequently a distraction frame, as is shown in FIG. 17, may be brought into connection with the rods 66, 68. The distraction frame 120 consists of a bolt 122 which is round in cross section and which in an end region comprises teeth 124. At the other end of the bolt 122 there sits a jaw 123 which is rigidly attached. A second jaw 126 is displaceable on the bolt 122 and comprises a latching mechanism 128 which can lockingly engage teeth 124 in order to fix the jaws 126 in a desired or selected position on the teeth 124.

The jaws 123, 126 comprise at the other ends receiving pieces 130 and 132 which extend coaxially towards one another and comprise receiving openings 134. The receiving piece 130 is rigidly connected to the jaw 123. The receiving piece 132 may be adjusted in its position towards or away from the receiving piece 130 with the help of a threaded spindle, not shown in FIG. 17, which is rotated via a knob 136. The receiving openings 134 accommodate the pegs 106, 108 or the rods 66, 68 so that with the help of the frame 120 a distraction force may be exerted onto the vertebrae 52, 54.

The operation procedure with the help of the represented instrumentation is as follows.

A rod 66 with the attachment 112 is introduced on a wire or other guide, not shown, which has been previously introduced. In this case two rods 66 are introduced for the attachment on the vertebrae. Thereafter the housing 56 is implanted after the soft parts have been brought out of the way. With this the U-shaped parts of the housing 56 are supported in the described way and manner on the rods 66 and in the assumed position are fixed by the described locking system 70. Before, an attachment of the housing 56 may be fastened to the vertebrae with the help of a wire which is wound through eyes 92. Subsequently the distraction frame 120 is connected to the rods 66 and a distraction is effected. Thereafter the resection of the diseased bone parts or invertebral disk and the dissection of the neighboring vertebra bodies takes place. After loosening the U-shaped parts of the housing 56 relative to one another, the distraction frame and the instrument 66 are removed. Thereafter there is effected the introduction of the vertebra plates 20. 22 in the above described way and manner, wherein they are firstly only fixed with one screw on the vertebra 52, 54. It is to be understood that one may also work without the instrument 66 in that right at the beginning the vertebra plates 20, 22 are introduced in the described way and manner and are screwed to the bone for the first distraction. After the introduction of the vertebra plates via the instrument 68 again with the help of the distraction frame 120 a distraction is carried out and an exact alignment of the vertebrae 52, 54 for the subsequent insertion of the stack formed by the cage-like bodies 10 to 16. Before this is effected the adjusting screw 46 is screwed into the middle body 12 in the manner shown in FIG. 2. At the end of the adjusting screw 46 there is provided a threaded bore into which there is screwed a threaded section 140 of a rod 142 which is connectable at the other end to the removable handle.

The instrument shown in FIG. 15 serves to introduce the stack formed by the bodies 10 to 16 between the vertebra plates 20, 22, while rods 68 are still connected to the vertebra plates 20, 22. At this point the distraction frame 120 and the rods 68 may be removed from the vertebra plates 20, 22. Into the second limb of the vertebra plates 20, 22 there is then screwed the second bone screw 28, in order to finally fasten the vertebra plates 20, 22. As soon as this is effected the connection and compression plate 32 is applied and fixed relatively loosely with the help of screws 42, 43. With the help of the adjusting screw 46 there is effected an alignment of the stack of the bodies 10 to 16. Thereafter by tightening the screw 42 a compression takes place and the bodies 10 to 16 are rigidly tensioned on one another.

Finally with the help of a hollow tubular rod 144 which at one end comprises a drive 146 for nut 51 and at the other end is connected to a handle 145, the nut 51 is fastened to the threaded section of the adjusting screw 46. The nut may be displaced over the rod 142 along with the hollow rod 144 and is subsequently tightened in order to rigidly connect the plate 32 to the adjusting screw 46. At this point the instruments shown in FIGS. 15 and 16, as well as the tunnel-like housing 56, may be removed and the implantation of the implant is completed.

What is claimed is:

1. An instrument for the positioning of an implant in the human spine, as a replacement for one or more vertebra bodies located between two healthy vertebra bodies, comprising:

a pair of vertebra body plates each attachable to a healthy vertebra body;

a pair of distraction rods, which at one end are attachable to one of said vertebra body plates;

two U-shaped parts, each having a pair of limbs forming the legs of the U, said limbs of each U-shaped part telescopically cooperate and form a tubular housing around the attached distraction rods, wherein the U-shaped parts comprise inner sections which are supported on the distractions rods; and a distraction instrument which is connected to the distraction rods for exerting a force onto the rods transversely to their longitudinal extension.

2. The instrument according to claim 1, wherein the vertebra plates have a first limb for bearing against an end surface of a healthy vertebra body and with a second limb which bears on the circumferential surface of said healthy vertebra body, wherein the second limb comprises a threaded hole for a connection to the distraction rod.

3. The instrument according to claim 2 for use with an implant having a side which faces a vertebra body and includes a receiving section for receiving said first limb and the receiving section being formed such that said implant may be inserted in a space from which said vertebra bodies have been removed while the vertebra plates are bearing against said healthy vertebra bodies.

4. The instrument according to claim 1, wherein the U-shaped parts have a wall which is curved outwardly in a circular arc shaped manner.

5. The instrument according to claim 4, wherein the walls have an inner side on which is mounted an attachment extending between the limbs of the U-shaped parts, said attachment having an opening to at least partly accommodate one of the distraction rods.

6. The instrument according to claim 1, wherein on one of said limbs of one of said U-shaped parts there is formed a row of recesses and on one of said limbs of the other of said U-shaped part there is a bar with a lateral peg which can be lockingly introduced into one of the recesses.

7. The instrument according to claim 6, wherein the recesses comprise a narrow section and the lateral peg comprises a non-circular elongate cross section rotatably mounted in the bar in a manner such that it may be inserted into and through a narrow section of one of the recesses only in a first rotational position and in a second wider rotational position can be locked in the recess.

8. The instrument according to claim 7, wherein the bar has two ends and at both ends comprises a rotatable non-circular locking peg and the lateral edges of the other U-shaped part likewise comprise at least one recess with a narrow section.

9. The instrument according to claim 1, wherein said U-shaped parts are formed such that they can be telescopically inserted into one another.

10. The instrument according to claim 1, wherein an introduction rod connectable to one of the vertebra plates serves as a distraction rods.

11. The instrument according to claim 10, wherein said distraction rod which can be releasably attached laterally on the implant.

12. The instrument according to claim 11, wherein the rods are connectable to a releasable handle.

13. The instrument according to claim 1, wherein the said implant comprises a stack of a least three cage-like annular bodies joined by a compression plate and an adjusting screw which is screwed into a middle body of said at least three bodies, said adjusting screw having an end screwed to the compression plate, wherein a threaded section of the adjusting screw extends through an elongate hole in the compression plate and an introduction rod can be brought into rotational engagement with said end of the threaded section and there is provided a hollow rod with a drive at one end for a nut which can be screwed onto the threaded section of said adjusting screw.

14. The instrument according to claim 1, wherein a distraction frame is provided with two jaws of which one is rigidly attached to a connection piece and the other jaw is moveable in steps with respect thereto, on the jaws there are attached receiving openings for the receiving of said distraction rods, wherein the one receiving opening on the moveable jaw is adjustable with respect to the rigid jaw.

15. The instrument according to claim 1, wherein said one of distraction rods has an inner end comprising an L-shaped plate formed by a pair of limbs with one limb of said L-shaped plate bearing against the end surface of the vertebra body and the other limb of the L-shaped plate bearing against the lateral wall of the vertebra body.

16. A method for replacing diseased vertebra located between two healthy vertebra with an implant, comprising:

attaching one of a pair of generally L-shaped guide elements to each of the two healthy vertebra, a first leg of the L-shaped guide element including a guide surface extending into a space between the healthy vertebra and the diseased vertebra;

attaching a rod to a second leg of each of the L-shaped guide elements, which leg extends along an outer surface of the healthy vertebra;

distracting said healthy vertebra by distracting said rods;

removing said diseased vertebra, creating a space between the healthy vertebra; and inserting an implant having guide surfaces into said space by using the guide surfaces on said L-shaped guide element to guide corresponding guide surfaces on said implant.

17. The method as set forth in claim 16 further including placing an expandable cover over said rods prior to distracting.

18. The method as set forth in claim 16, wherein said guide surfaces on said first leg of said L-shaped guide element and said implant are mating male and female guide tracks.

19. The method as set forth in claim 18, wherein said guide tracks are slideable rods having a dovetail shape.

20. A method for replacing diseased vertebra located between two healthy vertebra with an implant comprising:

attaching a rod to each healthy vertebra via an L-shaped plate, said L-shaped plate having a first leg including a guide surface extending into a space between a healthy vertebra and a diseased vertebra and a second leg fixed to an outer surface of said healthy vertebra;

distracting said healthy vertebra by distracting said rods;

removing said diseased vertebra creating a space between the healthy vertebra; and inserting an implant having a guide surface formed thereon into said space by using the guide surface on said first leg of said L-shaped plate to guide a corresponding guide surface formed on said implant.

21. The method as set forth in claim 20 further including placing an expandable cover over said rods prior to distracting.

22. The method as set forth in claim 21 wherein said cover is composed of two U-shaped parts that can be telescopically inserted into one another.

23. The method as set forth in claim 20, wherein said guide surfaces on said first leg of said L and said implant are mating male and female guide tracks.

24. The method as set forth in claim 23, wherein said guide tracks are slideable rods having a dovetail shape.

25. A system for replacing a diseased vertebra located between two healthy vertebra with an implant comprising:

a generally L-shaped plate coupled to each of the two healthy vertebra, said plate having a first leg, including a guide surface extending into a space between the healthy vertebra and the diseased vertebra and a second leg fixed to said healthy vertebra;

a rod coupled to said second leg of each of said generally L-shaped plates and extending outwardly from said healthy vertebra;

a distraction tool engageable with said rod coupled to each healthy vertebra for distracting said healthy vertebra to allow removal of the diseased vertebra;

an implant having guide surfaces formed thereon engageable with the guide surfaces on said first leg of said L-shaped plate to guide the implant into a space created by the removal of the diseased vertebral; and an expandable hollow cover sized to fit over said rods and surround said diseased vertebra.

26. The system as set forth in claim 25, wherein said expandable cover comprises two U-shaped parts that can be telescopically inserted into one other.

27. The instrument according to claim 26, wherein the U-shaped parts have walls, the walls have an inner side on which is mounted an attachment extending between the limbs of the U-shaped parts, said attachment having an opening to at least partly accommodate the rod.

28. The instrument according to claim 25, wherein said U-shaped parts have a limb on which there is formed a row of recesses and on the other U-shaped part there is a bar with a lateral peg which can be lockingly introduced into one of the recesses.

29. The instrument according to claim 28, wherein the recesses comprise a narrow section and the locking peg comprises a non-circular elongate cross section rotatably mounted in the bar in a manner such that it may be inserted into and through a narrow section of one of the recesses only in a first rotational position and in a second wider rotational position can be locked in the recess.

* * * * *

UNITED STATES PATENT AND TRADEMARK OFFICE
CERTIFICATE OF CORRECTION

PATENT NO. : 6,296,647 B1
DATED : October 2, 2001
INVENTOR(S) : Bernd Robioneck, Christian Lutz, Rainhard Windhager, Rainer Kotz, Richard Vlasak and Paul Wuisman It is certified that error appears in the above-identified patent and that said Letters Patent is hereby corrected as shown below:

Column 2,
Line 25, "are" (first occurrence) should read -- is --.
Line 31, "rib" should read -- rods --.

Column 5,
Line 35, after "26" insert -- , --.

Column 7,
Line 33, "distractions" should read -- distraction --.

Column 8,
Line 12, "rods" should read -- rod --.
Line 14, cancel "which".
Line 19, "a" (second occurrence) should read -- at --.
Line 37, after "wherein" insert -- one of --.
Line 37, cancel "one".
Line 38, cancel "of".

Column 9,
Line 25, "L" should read -- L-shaped plate --.

Signed and Sealed this

Sixteenth Day of July, 2002

*Attest:*

*Attesting Officer*

JAMES E. ROGAN
*Director of the United States Patent and Trademark Office*